United States Patent
Wolff et al.

(10) Patent No.: US 9,901,669 B2
(45) Date of Patent: Feb. 27, 2018

(54) METHOD AND APPARATUS FOR THE DETERMINATION OF AN INTERNAL FILTRATION DURING AN EXTRACORPOREAL BLOOD TREATMENT

(71) Applicant: B. BRAUN AVITUM AG, Melsungen (DE)

(72) Inventors: Henrik Wolff, Witzenhausen (DE); Christof Strohhoefer, Kassel (DE); Roland Napierala, Werther (DE)

(73) Assignee: B. BRAUN AVITUM AG, Melsungen (DE)

( * ) Notice: Subject to any disclaimer, the term of this patent is extended or adjusted under 35 U.S.C. 154(b) by 250 days.

(21) Appl. No.: 14/227,773

(22) Filed: Mar. 27, 2014

(65) Prior Publication Data

US 2014/0305869 A1    Oct. 16, 2014

(30) Foreign Application Priority Data

Apr. 16, 2013    (DE) .......................... 10 2013 103 816

(51) Int. Cl.
*B01D 63/00*    (2006.01)
*B01D 61/00*    (2006.01)
(Continued)

(52) U.S. Cl.
CPC ............ *A61M 1/3403* (2014.02); *A61M 1/16* (2013.01); *A61M 1/1601* (2014.02);
(Continued)

(58) Field of Classification Search
CPC .............. A61M 1/3621; A61M 1/1601; A61M 1/3417; A61M 1/3441; A61M 1/14
See application file for complete search history.

(56) References Cited

U.S. PATENT DOCUMENTS

| 4,381,999 A | 5/1983 | Boucher et al. |
|---|---|---|
| 5,580,460 A | 12/1996 | Polaschegg |

(Continued)

FOREIGN PATENT DOCUMENTS

| CN | 101010110 A | 8/2007 |
|---|---|---|
| CN | 101141989 A | 3/2008 |

(Continued)

OTHER PUBLICATIONS

Ingrid Ledebo et al; Hemodialfiltration—Optimal efficiency and safety, NDT Plus (2010) 3: 8-16, advance access publication Nov. 5, 2009.*

(Continued)

*Primary Examiner* — Ana Fortuna
(74) *Attorney, Agent, or Firm* — RatnerPrestia

(57) ABSTRACT

A method and apparatus for the treatment of blood are disclosed allowing for the determination of an internal convection in a blood purification device e.g. in the form of a dialyzer. The internal convection in the purification device can be determined on the basis of pressure differences in the purification device. The blood purification may be, for instance, a hemodialysis or a hemodiafiltration. Pressure sensors serve for measuring the pressures of the blood at the input and/or output of the purification device as well as optionally for detecting the pressure of a cleaning fluid or dialysis fluid at the input and/or output of the purification device.

13 Claims, 4 Drawing Sheets

(51) Int. Cl.
  *B01D 11/00* (2006.01)
  *C02F 1/44* (2006.01)
  *A61M 1/34* (2006.01)
  *A61M 1/16* (2006.01)
  *B01D 61/24* (2006.01)
  *B01D 61/32* (2006.01)
  *A61M 1/36* (2006.01)

(52) U.S. Cl.
  CPC ............ *A61M 1/1613* (2014.02); *A61M 1/34* (2013.01); *A61M 1/3406* (2014.02); *B01D 61/243* (2013.01); *B01D 61/32* (2013.01); *A61M 1/1607* (2014.02); *A61M 1/1609* (2014.02); *A61M 1/361* (2014.02); *A61M 2205/3331* (2013.01); *A61M 2205/3334* (2013.01)

(56) References Cited

U.S. PATENT DOCUMENTS

| | | | |
|---|---|---|---|
| 6,793,827 B1* | 9/2004 | Bosetto | A61M 1/1656 210/134 |
| 7,131,956 B1 | 11/2006 | Pirazzoli et al. | |
| 7,131,957 B2* | 11/2006 | Muller | A61M 1/16 210/321.71 |
| 7,879,241 B2* | 2/2011 | Sparks | A61M 1/1656 210/321.71 |
| 2008/0215247 A1* | 9/2008 | Tonelli | A61M 1/16 702/19 |
| 2008/0251433 A1 | 10/2008 | Kim et al. | |
| 2010/0042035 A1* | 2/2010 | Moissl | A61M 1/16 604/5.04 |
| 2010/0089817 A1 | 4/2010 | Heilmann et al. | |
| 2012/0095381 A1 | 4/2012 | Tonelli et al. | |
| 2013/0134077 A1 | 5/2013 | Wieskotten et al. | |
| 2013/0303961 A1 | 11/2013 | Wolff et al. | |

FOREIGN PATENT DOCUMENTS

| | | | |
|---|---|---|---|
| DE | 27 45 348 | 4/1978 | |
| EP | 0 240 101 | 10/1987 | |
| EP | 1175917 A1 * | 1/2002 | ............ A61M 1/16 |
| EP | 1 867 353 | 12/2007 | |
| WO | WO 2012/095066 | 7/2012 | |

OTHER PUBLICATIONS

Landis et al., "Exchange of substances through the capillary walls," Handbook of Physiology—Section 2: Circulation, 11 (1963); pp. 961-1034.

Wuepper et al., "Retrofiltration rates in high-flux hollow fiber hemodialyzers: analysis of clinical data," Journal of Membrane Science, 121 (1996); pp. 109-116.

Chinese Office Action for Chinese Application No. 201410143527.X, dated Mar. 1, 2017, including English translation, 13 pages.

* cited by examiner

METHOD AND APPARATUS FOR THE DETERMINATION OF AN INTERNAL FILTRATION DURING AN EXTRACORPOREAL BLOOD TREATMENT

CROSS REFERENCE TO RELATED APPLICATIONS

This application claims priority to German application DE 10 2013 103 816.6 filed Apr. 16, 2013, the contents of such application being incorporated by reference herein.

FIELD OF THE INVENTION

The invention relates to a method and an apparatus in particular for the determination of an internal filtration during an extracorporeal blood treatment such as a dialysis, i.e. a blood purification process.

DESCRIPTION OF THE RELATED ART

From EP 0 240 101 A2 there is known a dialysis apparatus comprising a filter (dialyzer) and a membrane within a sealed chamber. The inlet and the outlet of the filter are each provided with a pump, the blood flow rate being calculated on the basis of the rotational speeds of the pumps. In addition, one of the pumps is controlled in such a manner that a specific discharge rate is met and a desired average transmembrane pressure is maintained.

BACKGROUND OF THE INVENTION

Basically, the internal filtration which is also referred to as an internal convection cannot be measured outside the dialyzer, but is of great interest in order to quantify the convective purification performance of a blood treatment such as a blood purification therapy, e.g. a hemodialysis therapy.

SUMMARY OF THE INVENTION

The invention relates to an object of allowing for a determination of an internal convection during a blood treatment, and to control, for instance, the internal convection during the treatment. A further aim is to display the determined internal convection to the user preferably online.

In one or more or all of the exemplary embodiments, displaying the determined internal convection may be provided in addition.

In one or more or all of the exemplary embodiments, a method of purifying blood is implemented, in which the blood is conveyed through a purification device serving as a filter device, optionally in the form of a dialyzer, and the internal convection in the purification device is determined e.g. on the basis of pressure differences in the purification device.

The blood purification may be a hemodialysis or a hemodiafiltration, for example. Pressure sensors may be provided for measuring the pressures of the blood at the input and/or output of the purification device. Optionally, pressure sensors may also be provided for detecting the pressure of a cleaning fluid such as a dialysis fluid at the input and/or output of the purification device. As an alternative to this, the flows of a cleaning fluid and/or of the blood may be determined outside the body and the pressure differences can be determined on the basis thereof by calculation or with the aid of characteristic curves or value tables which are specific to the dialyzer and have been stored in advance.

A determination of hematocrit or a determination or presetting of a plasma viscosity or a plasma protein concentration may be carried out in addition. It is also possible to determine two or all three of these values.

Further, a median transmembrane pressure can be calculated for the filtration with the aid of determined pressures and a pressure intersection made up of the blood pressure profile and the cleaning fluid pressure profile, preferably the dialysis fluid pressure profile, can be determined. The internal convection may be calculated e.g. on the basis of the transmembrane pressure and possibly additionally in consideration of an ultrafiltration coefficient as a product of the filter surface and the permeability. The characteristic filter parameter "transmembrane pressure" is not required for the internal filtration, but may be used, for example, as a test parameter for the monitoring of the ultrafiltration coefficient $K_{UF}$.

The determined internal convection (convective filtration) may optionally be controlled, too, preferably by comparing a determined value of the internal filtration with a predefined target value and adapting the flow of the blood to be purified and/or the flow of the cleaning fluid such as the dialysis fluid.

In one, more or all of the exemplary embodiments, an apparatus is further provided for an extracorporeal blood treatment, e.g. for purifying blood, comprising a purification device through which blood can flow, preferably in the form of a dialyzer, and a determination device for determining an internal convection in the purification device on the basis of pressure differences in the purification device.

The apparatus may be designed for hemodialysis or hemodiafiltration and be provided with pressure sensors for measuring the pressures of the blood at the input and/or output of the purification device. Optionally, one or more pressure sensors may be provided for detecting the pressure of a cleaning fluid, for instance of a dialysis fluid, at the input and/or output of the purification device.

The determination device may further be designed for a hematocrit determination or hematocrit presetting and/or may be able to effect a determination or presetting of a plasma viscosity or a plasma protein concentration.

The device may further be designed to calculate a median transmembrane pressure for the filtration with the aid of determined pressures; to determine a pressure intersection made up of the blood pressure profile and the cleaning fluid pressure profile, preferably the dialysis fluid pressure profile; and/or to calculate the internal convection on the basis of the blood pressure profile and the cleaning fluid pressure profile and/or the transmembrane pressure and possibly also in consideration of an ultrafiltration coefficient as a product of the filter surface and the permeability.

In one, more or all of the exemplary embodiments, the apparatus may be equipped with a control unit which is designed to control the determined convective filtration, preferably by comparing a determined value of the internal convection with a predefined target value and adjusting the flow of the blood to be purified and/or the flow of the cleaning fluid such as the dialysis fluid.

One or more exemplary embodiments of the invention allow for a determination of an internal filtration or convection within a blood purification device such as a dialyzer while carrying out the blood purification, for instance the hemodialysis, i.e. quasi online. This allows for quantification of the convective purification performance of the blood purification such as of the hemodialysis therapy. Thus, calculating the internal convection is possible during the treatment.

Furthermore or in addition, one or more exemplary embodiments allow for control of the internal convection during the treatment.

In one or more exemplary embodiments of the invention it is possible to indicate e.g. the internal filtration as a current flow rate as well as optionally in addition or as an alternative the previous volume of the filtration or of the cleaned blood or of the dialysis fluid and possibly also an expected value of this volume at the end of the therapy. Here, a conversion into the clearance, i.e. the achieved purification, is also possible, if this is desired. This indication of the internal filtration may occur during carrying out the blood purification such as the hemodialysis, i.e. online, so to speak. Further, it is possible to perform an adaptation of parameters of influence, for instance on the basis of a measuring signal during the ongoing treatment, i.e. again "online", with these parameters having an impact on the internal convection and the filtration. Said adaptation of the parameters of influence such as e.g. the flow rate of the blood or e.g. the dialysis fluid, the temperature or the like may be carried out, for example, by means of a corresponding adjustment of the blood flow or of the dialysis fluid flow and/or also via a pressure change on the blood side, or through changing the temperature of the dialysis fluid. The pressure shift on the blood side produces a phase resulting from the filtration and then a phase resulting from a back-filtration. It is further possible to show the current volume during the ongoing treatment and/or the current flow rate of the blood e.g. on a monitor or a pointer instrument or to represent said variable(s) in a different visual or acoustic form or any other form.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
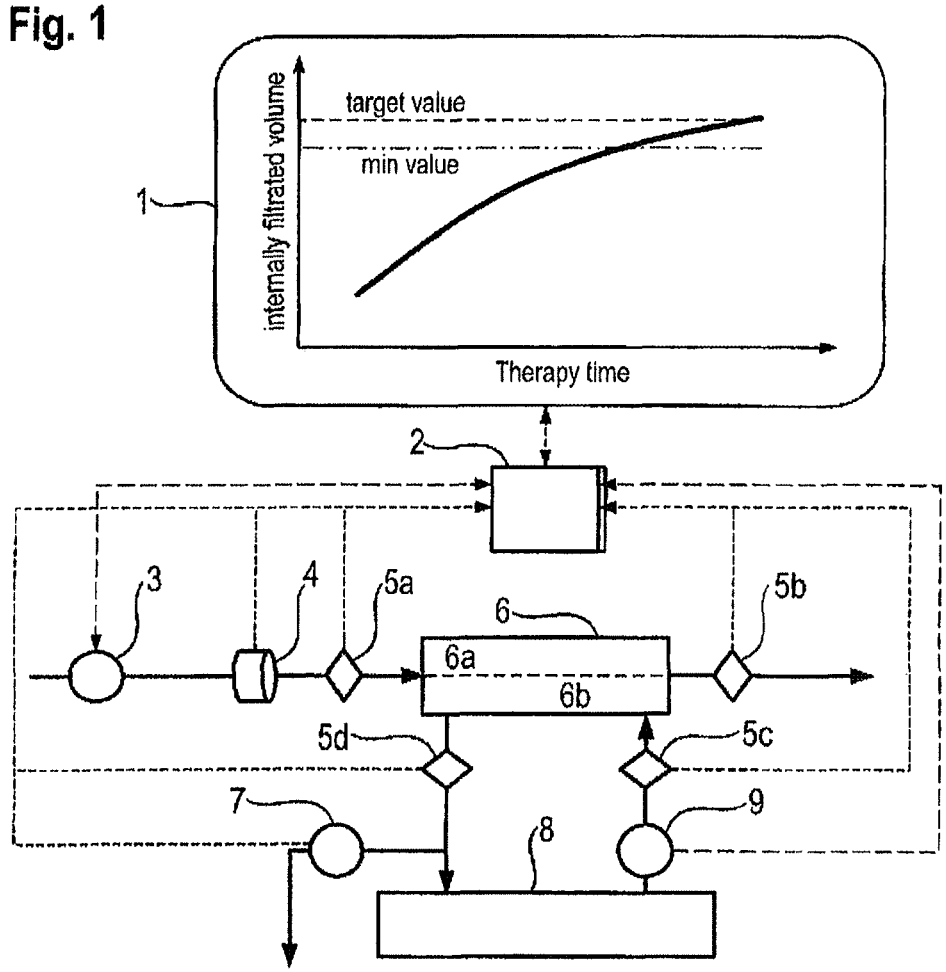
FIG. 1 shows a schematic configuration of an exemplary embodiment of the apparatus according to aspects of the invention.

FIG. 1 shows an exemplary embodiment of an apparatus (equipment) according to aspects of the invention, comprising a dialyzer 6 having a blood chamber 6a and a dialysis fluid chamber 6b. The blood to be cleaned is supplied by means of a blood pump 3 and delivered to the dialyzer 6 through a sensor 4 for the determination of a blood parameter such as for determining the hematocrit. Pressure sensors 5a, 5b at the input and output of the dialyzer 6 detect the pressure of the blood at the input and output of the dialyzer, respectively.

A balance system 8 carries out a balancing process on the basis of the dialysis fluid which is fed through a dialysis fluid pump 9 to the dialysis fluid chamber 6b. The input-side pressure of the dialysis fluid at the input of the dialysis fluid chamber 6b is measured by a pressure sensor 5c. A further pressure sensor 5d detects the pressure of the dialysis fluid when it leaves the dialysis fluid chamber 6b. The dialysis fluid which has left the dialysis fluid chamber 6b is supplied to the balance system 8 and is transported to an outlet or waste container, additionally or alternatively via an ultrafiltration pump 7, as is illustrated by the arrow.

A control unit 2 receives the current values of all pressures and flows and, if any, further blood parameters such as a determined/input hematocrit value, as is illustrated by the dashed lines. If required, the control unit 2 sets new values for the blood flow and/or the dialysis fluid flow and activates the blood pump 3 and the dialysis fluid pump 9 as well as the ultrafiltration pump 7 in corresponding fashion. A display 1 shows e.g. the calculated parameters, for example in the form of a graphic diagram, as it is illustrated in FIG. 1 in block 1. It is further possible to input preset values and target values for the control unit 2 on or in the display 1 by actuating corresponding buttons or by corresponding input actions. The display 1 may be equipped with a memory and/or processor or may be connected thereto, calculating the corresponding evaluations and being capable of calculating target variables for the pump control and other control systems.

On the basis of the parameters (i.e. the specification) of the blood purification device which is employed in each case, such as of the dialyzer 6, the following calculations can be carried out. These parameters include the geometrical parameters such as the dialyzer surface, the volume, the fiber length as well as the inner diameter, the outer diameter and the number of the fibers etc. of the dialyzer as well as the permeability for filtration and back-filtration. Further, the characteristic curves are of interest, establishing an interrelation between the blood flow and the dialysis fluid flow, on the one hand, and the produced internal convection on the other hand.

Figure 2:
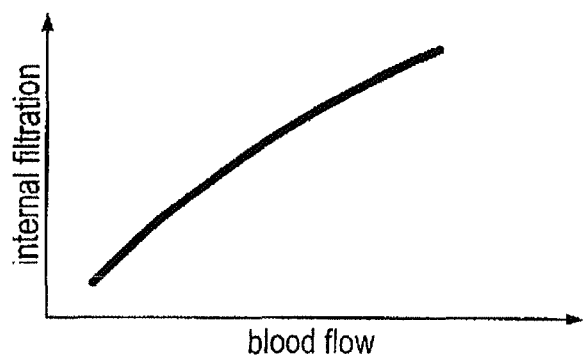
FIG. 2 illustrates the internal filtration versus the blood flow for an exemplary embodiment.

FIG. 2 schematically shows a graphic illustration of a characteristic curve, where the blood flow, i.e. the blood flow in ml/min is plotted on the abscissa, and the extent of the internal filtration is plotted on the ordinate. The characteristic curve has a substantial linear course with a decreasing gradient for higher blood flows. It goes without saying that according to the dialyzer 6 which is employed in each case, the characteristic curve may also have a different course but one which is known in advance.

Figure 3:
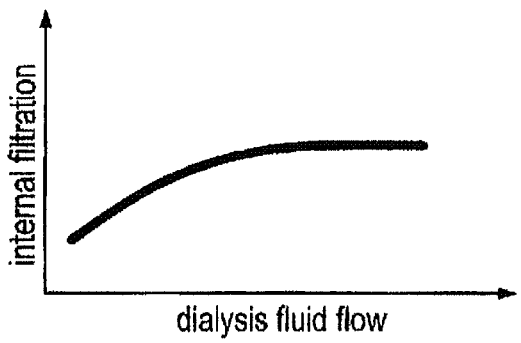
FIG. 3 shows a diagram for the internal filtration as a function of the dialysis fluid flow.

FIG. 3 illustrates a graphic illustration of the interrelation between the dialysis fluid flow (abscissa) and the internal filtration (ordinate). As can be taken from FIG. 3, the internal filtration increases much more slowly in case of a higher dialysis fluid flow and asymptotically approaches a limit value after a relatively short time.

It can be seen in FIGS. 2 and 3 that the dependency of the internal filtration on the dialysis fluid flow shows a much stronger non-linear behavior than the dependency of the filtration on the blood flow (FIG. 2). This circumstance is due to various reasons. In an ideal system, the blood-sided pressure drop increases linearly with the blood flow, being reflected in a linear gradient of the internal filtration. On the other hand, an intensified filtration flow over the filter membrane causes internal changes, so that the dependence is not strictly linear in reality.

If, however, the pressure drop on the dialysis fluid side is enhanced by an increased flow of the dialysis fluid while the blood flow is kept constant (the crucial point is the progressive concentration of substances such as cells or proteins which are not able to permeate the membrane), a zone will be reached in which an excessively high amount of plasma water is taken away from the blood within the fibers. What is more, the stronger progressive concentration of blood cells and proteins will provoke a clogging of the dialyzer 6. Hence, the blood flow is the limiting factor in this case.

The dialyzer 6 should preferably have a packing density of more than 50%, so that there is a sufficiently high flow resistance on the dialysis fluid side. In this case, the pressure drop can be controlled by a sufficiently high change in the flow of the dialysis fluid.

Figure 4:
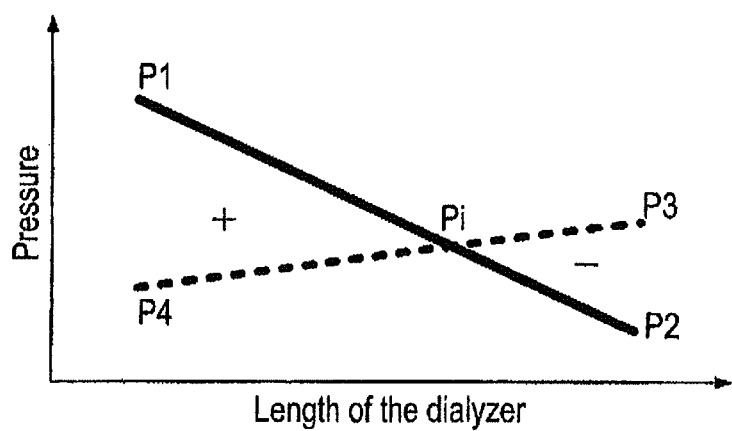
FIG. 4 shows a graphic illustration of pressure curves in the dialyzer on the blood side and on the dialysis fluid side for an exemplary embodiment without using a hematocrit value.

FIG. 4 shows a pressure diagram in which the pressure is shown on the ordinate. The abscissa shows the length of the dialyzer or the respective position in the dialyzer. The pressure curve of the blood is shown with a solid line, with a pressure P1 prevailing upon entering the dialyzer and a lower pressure P2 prevailing on the blood exit side of the dialyzer 6. The pressure curve of the dialysis fluid flowing in countercurrent is represented in FIG. 4 with a dotted line, starting from a lower pressure P4 prevailing at the dialysis fluid exit side up to a higher pressure P3 occurring at the dialysis fluid entry side. The two pressure lines intersect at a point Pi. Ahead of this intersection, the pressure on the blood side is larger than that on the dialysis fluid side. To the right of the pressure Pi, this fact is inversed. This results in the pressure intersection illustrated in FIG. 4, assuming and performing a linearized calculation. On this basis, the respectively achieved internal filtration can be measured and detected during the treatment and hence can be processed and output, as it were, in "online" fashion. In FIG. 4, the area between the two pressure lines on the blood side and the dialysis fluid side to the left of Pi is provided with the symbol "+" to indicate that in this area the pressure of the blood is larger than that of the dialysis fluid. In the area between the two pressure lines to the right of the intersection Pi, there is to be seen the symbol "−" to make clear that here the pressure on the blood side is lower than that on the dialysis fluid side.

On the basis of the pressure intersection shown in FIG. 4, formed from the blood pressure and the dialysis fluid pressure, the median transmembrane pressure for the filtration can be calculated from the pressures P1, P2, P3, P4, Pi. In one or more exemplary embodiments, P1, P2, P3 are measured and P4 and Pi are calculated. P4 depends on the pressure drop on the dialysis fluid side and can be calculated if the flow as well as the dialyzer or the geometry of the dialyzer are known. If the flow and the dialyzer 6 are known, a stored table may also be used to indicate the pressure drop. As an alternative, taking a measurement with an additional pressure sensor is also possible, of course.

The inclusion of online measurements of the pressures is advantageous, as these and consequently also the pressure intersection might change during a therapy. This means that the pressure intersection is calculated again for any point in time or for particular, discrete points in time during the therapy.

If it happens, for example, that some fibers are congested through local coagulation, also referred to as clotting, the pressure drop between P1 and P2 rises, and a so-called secondary membrane forms through the interaction of the blood components with the membrane. Furthermore, the pressure at the side of the dialysis side typically drops in order to maintain the ultrafiltration rate. The pressure drop on the dialysis fluid side does not change. This means that one pressure measuring point is still sufficient there, the other one can be determined. However, not the absolute pressures are decisive for the internal filtration, but the relative pressures from the blood side to the dialysis fluid side, i.e. the transmembrane pressure. This pressure gradient provides for the fluid flow over the membrane.

As the transmembrane pressure for the filtration is defined to be positive, this area is designated with "+". The formula reads:

$$TMP_+ = \frac{P1 + Pi}{2} - \frac{Pi + P4}{2} \quad \text{Equation 1}$$

In the event of a higher dialysis fluid pressure, the transmembrane pressure is defined to be negative. The formula reads:

$$TMP_- = \frac{P2 + Pi}{2} - \frac{Pi + P3}{2} \quad \text{Equation 2}$$

On this basis, the convective flow or "the filtration" can be calculated in one or more exemplary embodiments if the ultrafiltration coefficient, the product of filter surface and permeability ($K_{UF}=A*p$), is known.

Here, $K_{UF+}$ represents the ultrafiltration coefficient in the area of the positive transmembrane pressure.

$$Q_+ = K_{UF+} * TMP_+ \quad \text{Equation 3}$$

The same applies to the backfiltration in the area of the negative transmembrane pressure.

$$Q_- = K_{UF-} * TMP_- \quad \text{Equation 4}$$

In one or more exemplary embodiments, $K_{UF+}$ and $K_{UF-}$ are stored in a table for the respective dialyzer 6.

As the filtration differs from the backfiltration by the weight loss, i.e. the liquid which has been actually removed from the patient for dewatering, one has $$|Q_+| = |Q_-| + |Q_{WL}| \quad \text{Equation 5}$$

All the flow variables which have been shown can be indicated in different units. A typical unit is ml/min, but units such as e.g. ml/h, l/h, ml/therapy, l/therapy are also possible. This principle is basically intended for HD therapies, but may also be used in case of an HDF or a single-needle therapy. Here, HD represents hemodialysis and HDF represents hemodiafiltration.

A calculation with inclusion of further parameters will be described in the following.

The internal filtration changes, for instance, the hematocrit (Hct) within the dialyzer. This has a direct impact on the viscosity (A. Wiipper, D. Woermann, F. Dellanna, and C. A. Baldamus: Retrofiltration rates in high-flux hollow fiber hemodialyzers: Analysis of clinical data—Journal of membrane Science, 121:109-116, 1996)

$$\eta_B = \eta_P(1 + 2.5Hct + 7.35Hct^2) \quad \text{Equation 6}$$

Here, $\eta_B$ represents the viscosity of the blood and $\eta_P$ is the viscosity of the blood plasma.

The latter may be calculated for instance according to the following equation:

$$\frac{\eta_P}{\eta_W} = 1 + \left\{\frac{\eta_{P,R}}{\eta_W} - 1\right\} \cdot \left\{\frac{c_P}{c_{P,R}}\right\} \quad \text{Equation 7}$$

Here, $\eta_{P,R}$ is the reference value of the plasma viscosity, $c_{P,R}$ is the plasma protein concentration of the reference solution, $\eta_W$ is the viscosity of water, $\eta_P$ the viscosity of the plasma, $c_P$ is the current plasma protein concentration and Hct represents the hematocrit. The reference values $\eta_{P,R}$ and $c_{P,R}$ are stored as a standard, but may also be recorded specifically for each patient and then be stored.

In addition, the flows on the blood side and on the dialysis fluid side will change as a function of the local filtration.

Figure 5:
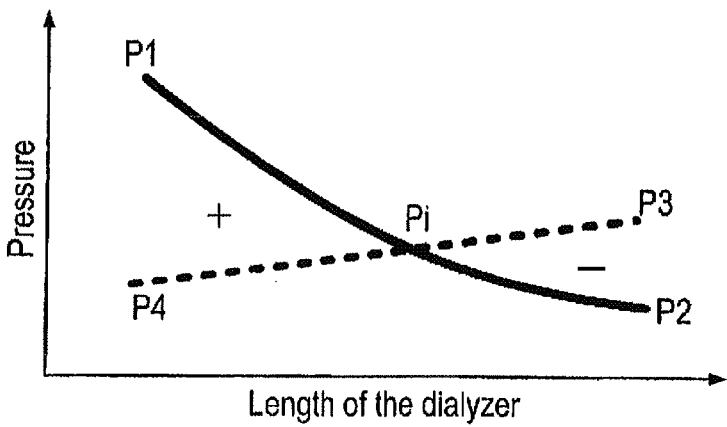
FIG. 5 illustrates pressure curves within the dialyzer for the blood side and the dialysis fluid side for an exemplary embodiment using a hematocrit value.

Thus, it is possible to calculate a curve of the pressures within the dialyzer 6 which deviates from linearity and shows a somewhat more accurate reflection of the actual processes within the dialyzer. This is shown in FIG. 5 for which the same explanations are true as for FIG. 4. The blood pressure curve is not linear here.

With these conditions, too, the median transmembrane pressure for filtration and backfiltration can be determined in consideration of the curve profile and the respective flows can be calculated.

In addition, the oncotic pressure, i.e. the amount of the osmotic pressure which is caused by the colloids of a solution, can be calculated with the aid of the hematocrit values (Hct value) detected by a hematocrit sensor; this oncotic pressure will not be detected at the measuring points outside the dialyzer 6. It is calculated according to (E. M. Landis and J. R. Pappenheimer: Exchange of substances through the capillary walls—Handbook of Physiology—Section 2: Circulation, 11:961-1034, 1963):

$$\Pi = 2.1 \cdot c_P + 0.16 \cdot c_P^2 + 0.009 \cdot c_P^3 \quad \text{Equation 8}$$

These facts form the basis of the curve profile according to FIG. 4.

Typically, the oncotic pressure is subtracted from the blood-sided pressure curve. However, an addition on the dialysis fluid side is also possible.

All initial values for pressure, hematocrit, plasma protein concentration, the reference values and further usable variables which are not mentioned here can be ascertained by measuring technology or transferred from a table stored on or in the apparatus or can be calculated.

In one or more exemplary embodiments of the invention, a calculation of the course of a parameter is performed, e.g. of the pressure curves or also of the internal filtration or any other dependent variables within the dialyzer 6.

Figure 6:
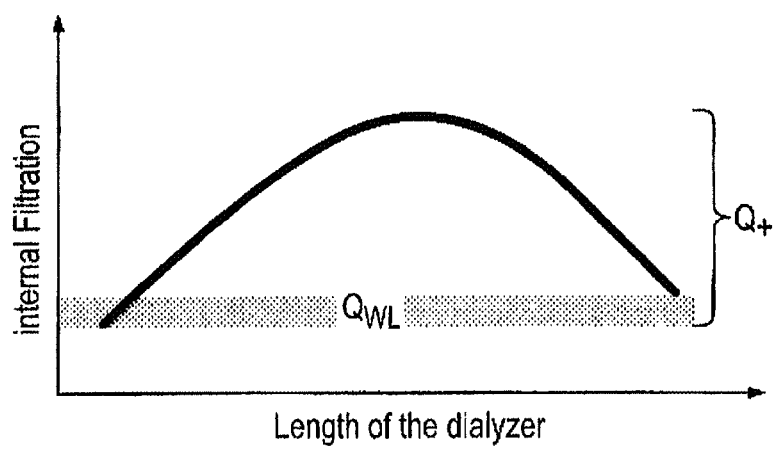
FIG. 6 illustrates a curve of the internal filtration over the length of the dialyzer.

FIG. 6 shows an example of this calculation of the curve within the dialyzer 6. Here, the internal filtration is taken as an example. On the basis of the pressure curves which are determined by the pressure sensors 5a to 5d (FIG. 1), a profile of the internal filtration or also a profile of any dependent variable such as e.g. the blood flow or dialysis fluid flow, of the hematocrit, of the viscosity of the blood or other parameters or a combination of these parameters or even the entirety of all such parameters can be established.

In the example shown in FIG. 6, the abscissa shows again the length of the dialyzer, i.e. the respective position within the dialyzer 6, whereas the ordinate shows the internal filtration. As can be seen, the internal filtration in the interior of the dialyzer 6 is higher according to expectation and has a curved shape with a maximum existing somewhat above the middle of the dialyzer 6, whereas the minimum is at the left dialyzer end, i.e. at the dialyzer inlet. The entire filtration span, starting from the filtration minimum on the left to the filtration maximum existing on the right, is indicated at the right end of the diagram of FIG. 6 with "$Q_+$". $Q_{WL}$ illustrates the band between the inlet-side and the dialyzer outlet-side filtration value.

In one or more exemplary embodiments of the invention, an adaptation of the calculated filtration is possible. If, for instance, the pressures change over the course of the therapy, this can be detected by means of the pressure sensors 5a to 5d. Said change in one or more of the pressures can then be taken into consideration in the calculation of the respective parameter, e.g. of the curve of the filtration within the dialyzer 6.

If, for instance, the ultrafiltration coefficient changes due to an interaction between the blood components and the membrane of the dialyzer 6, also this change in the ultrafiltration coefficient can be determined and considered. Due to a change in the flow rate, with which the patient being treated loses liquid, for instance the weight loss rate or ultrafiltration rate, a concomitant change in the transmembrane pressure TMP can be observed and detected. From this, the new ultrafiltration coefficient can be determined in analogy to the equations 3 and 4 indicated above and from this the new filtration can be detected and defined. If the ultrafiltration is constant, an alteration of the transmembrane pressure TMP can be ascertained and used for correcting the ultrafiltration coefficient $K_{UF}$. It is not directly the TMP which is required here, but rather the $K_{UF}$ value.

In the same way, it is also possible here to introduce a new initial hematocrit or any other variable which is measured during the therapy into the calculation. This allows to further refine the calculation or even to establish another variable. In consideration of a screening coefficient regarding specific molecules, which can be taken for example from a data sheet, a convective clearance for various substances can be specified, too.

In one or more exemplary embodiments of the invention, the internal filtration is adapted during the treatment of the patient, i.e. "online". To this end, it is preferred to have an effect on the surface area between the pressure curves, see e.g. FIGS. 2, 3, 4. This allows for the control of the internal filtration. The processes of influencing and determining the nature of the pressure curves are preferably carried out in good approximation by an orientation to the law of Hagen-Poiseuille, according to which the pressure drop is proportional to the respective flow.

A higher pressure drop increases the surface areas between the pressure curves on the blood side and dialysis fluid side and hence the values $TMP_+$, $TMP_-$ which are symbolized in FIGS. 4 and 5 with the symbol "+", "−", respectively. Thus, in one or more exemplary embodiments of the invention, the blood flow and/or the dialysis fluid flow is/are operated or controlled so as to reach e.g. a target value or to obtain a minimum value.

In one or more exemplary embodiments of the invention, the process of balancing may be disturbed for a short time, for instance by closing a venous shutoff clip in the blood return flow to the patient, and thus a higher filtration flow rate can be produced which is compensated for by an adaptation of the pressure on the side of the dialysis fluid. To this end, it is possible e.g. to activate the dialysis fluid pump 9 in a boosted manner for a short time, with the increased pressure generated thereby being detected by the pressure sensor 5c. Furthermore, a repeated process of closing may be carried out, for example via the venous shutoff clip, creating a pulsation. As an alternative or in addition, it is also possible to close a valve in the dialysis fluid outflow (to the left on the outlet of the ultrafiltration pump 7 according to FIG. 1), in fact once and for a short time or preferably several times, in order to have a short-term disturbing effect on the balancing.

Further, the pressure ratio can be influenced by applying an external negative pressure. For this purpose, e.g. the ultrafiltration pump 7 may be used, for instance by activating it in a boosted manner in order to create a negative pressure in the dialysis fluid chamber 6b.

In one or more exemplary embodiments of the invention, it is also possible to use the backfiltration as the control variable in addition to or as an alternative to the measures set out above.

In one or more exemplary embodiments of the invention, the current value of the filtration, for example, may be output on the display 1 according to FIG. 1. In doing so, it is possible to display the curve profile illustrated in FIG. 7 on the monitor of the display 7, showing at any point in time of the therapy the volume which has already been filtered.

Figure 7:
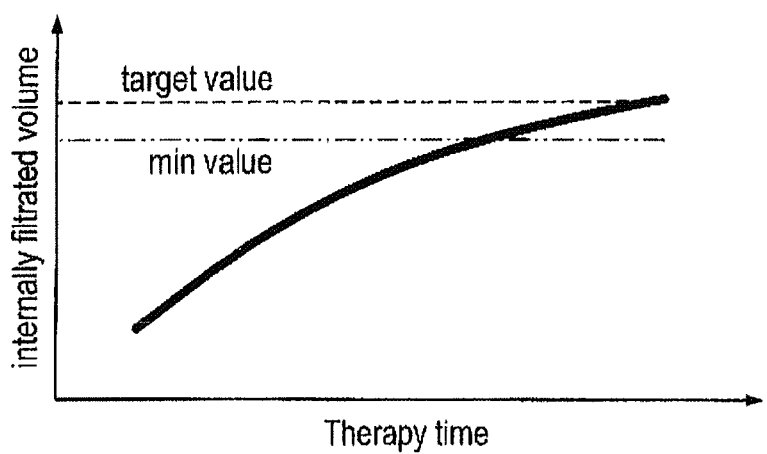
FIG. 7 shows a graphic illustration of a possible curve of an internal filtered volume throughout the therapy time.

The abscissa in FIG. 7 shows the therapy time, i.e. the time which has elapsed in each case since the beginning of the therapy, whereas the ordinate shows the internally filtrated volume in each case. The continuously rising curved line illustrates the filtrated volume. Further, FIG. 7 shows two horizontal broken lines, the upper one of which illustrates the optimum target value which can be reached, signalizing the full therapy success. The lower, dot-and-dash line represents the minimum value which should be reached at the minimum for a sufficient therapy. By reference to the curve representation according to FIG. 7, it can be directly seen on the display 1 how far the therapy has already proceeded and which therapy time is still to be expected. Further, any unexpected therapy curves can be immediately identified and suitable countermeasures can be taken.

As an alternative or in addition, the display 1 may also show the change in the flow (in the form of volume per unit of time).

The previous therapy progress (which can be seen on the display 1 or is stored in the apparatus), as of the beginning of the treatment until the current point in time, can also be used for a calculation and prediction of the further course. This also allows for the representation of the expected therapy progress as of the current point in time of the treatment until its end as a prediction of the further progress. This shows the user if and when the desired target is reached by the end of the therapy.

For the purpose of predicting the therapy progress, it is also possible to additionally use data from preceding therapies which has been registered or stored in any other way. On the basis of such data, conclusions can be drawn as to the expectable future progress by means of suitable evaluation and prediction programs.

Figure 8:
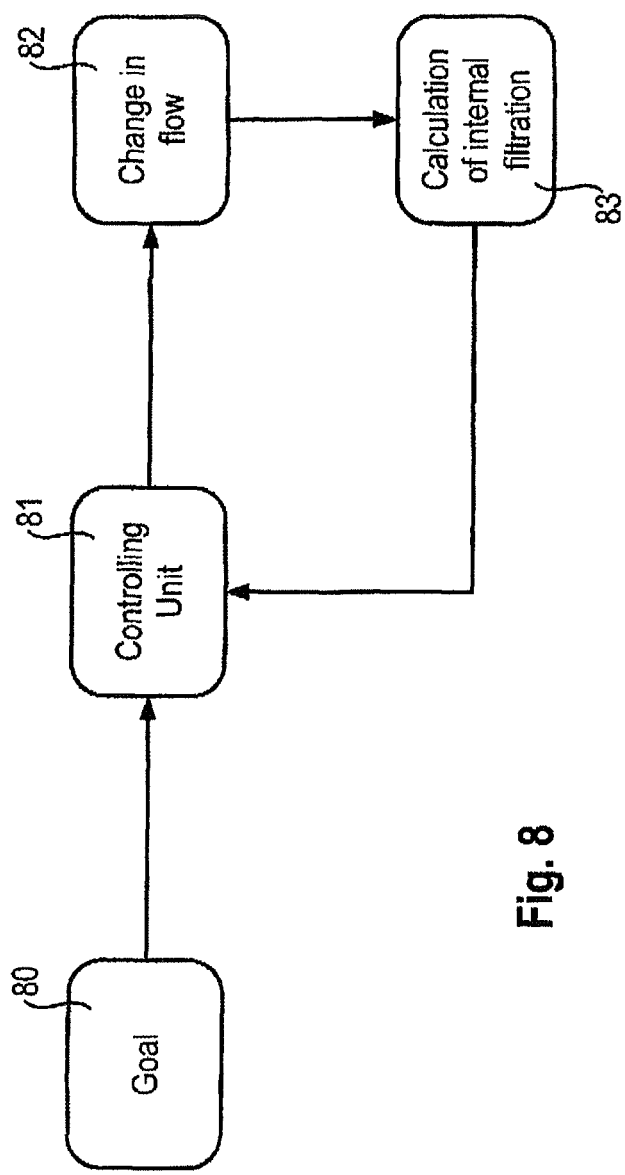
FIG. 8 illustrates an exemplary embodiment of a method according to aspects of the invention or an apparatus according to aspects of the invention.

FIG. 8 illustrates a block diagram of an exemplary embodiment of a control loop and a control system which can be used with exemplary embodiments of the method of the invention and the apparatus according to aspects of the invention.

A goal or input means 80, which may be implemented as a method feature or as a physical device, serves for inputting the target value which is desired in each case, see for instance the target value entered in FIG. 7. A controlling unit 81 compares the current value of the filtration, as it has been determined for instance by means of a calculation of the internal filtration, with the target value according to the input means 80. The controlling unit 81 may correspond to the control unit 2 according to FIG. 1, for example. The current value of the internal filtration is determined by a calculation device 83 or a corresponding calculation step, determining the value of the respective internal filtration for instance on the basis of the preceding embodiments. In the event of any deviations between the current value of the internal filtration, as it has been determined by the device 83 or the corresponding calculation step, and the target value according to the input means 80, the controlling unit 81 correspondingly adapts e.g. the blood flow and/or the dialysis fluid flow by provoking a change in the flow. This is illustrated by the block 82. Such change in the blood flow and/or dialysis fluid flow may be effected e.g. according to the above explanations by the blood pump 3, the dialysis fluid pump 9 and/or the ultrafiltration pump being changed in terms of their activation scheme.

The target variable, i.e. the target value which is input via the device 80 or the corresponding step, may be a flow rate in ml/min, ml/h, ml/therapy, . . . etc., for example.

With one or more exemplary embodiments of the apparatus according to aspects of the invention and of the method of the invention, it is thus possible to achieve a control of the internal filtration and backfiltration.

Accordingly, the exemplary embodiments of the invention allow to obtain knowledge of the internal filtration and hence of the convective purification performance during the therapy, i.e. the hemodialysis, hemodiafiltration or the like. This further allows for the control of the convective and thus the medium molecular clearance.

In the following, a specific exemplary embodiment is described on the basis of a numerical example; such numerical values, however, are not meant to be understood as a limitation.

According to an exemplary embodiment of the invention, the user—during the preparation of the dialysis treatment—selects e.g. a lower limit for the volume of 12 l which is to be produced by internal filtration by the end of the therapy.

At the beginning of the therapy, the hematocrit at the input of the dialyzer 6 and the pressures on the blood side as well as on the dialysis fluid side are measured. These values form the basis for calculating the course of the pressure curves within the dialyzer 6 in consideration of the oncotic pressure. For a measured hematocrit of 32%, for instance, the permeability for filtration amounts to 90 ml/(h mmHg m$^2$) and the permeability for backfiltration amounts to 265 ml/(h mmHg m$^2$).

The current internal filtration rate is calculated and amounts to e.g. 56 ml/min.

During the first hour of the treatment, the characteristics of the dialyzer as well as the pressures at the dialyzer 6 will change. The newly calculated internal filtration rate amounts only to e.g. 48 ml/min. Due to the falling tendency, the prediction for the achieved, internally filtrated volume is 11 l now.

The user is recommended, for instance via the display 1 or an acoustic output, to increase the dialysis fluid flow from 400 ml/min to 500 ml/min, in order to create larger local transmembrane pressures TMP+ and TMP− by means of the higher pressure drop on the dialysis fluid side which has been achieved by said increased flow and again increase the internal filtration rate thereby.

Having adapted the dialysis fluid flow, the internal filtration rate is calculated again and amounts to e.g. 52 ml/min.

During the next three hours of treatment, no further changes will appear and an internally filtrated volume of 12.4 l is achieved.

According to a further example, the user selects—during the preparation of the dialysis treatment—a lower limit for the online measurement of the medium molecular clearance of e.g. 70 ml/min. In this exemplary embodiment, the apparatus sets a value of e.g. 75 ml/min as an alarm limit for obtaining the desired clearance.

After the beginning of the therapy, the first measurement will be made and the result is 83 ml/min, for example.

After a therapy time of 90 min, the user is informed with a message on the monitor 1 of the dialysis apparatus that the medium molecular clearance is at 75 ml/min now and will probably continue to fall. It is recommended, e.g. in a visual way through the display or by acoustic ways and means, to increase the blood flow from 300 ml/min to 330 ml/min. Due to the adaptation of the flow, the next measured value for the medium molecular clearance amounts to 82 ml/min.

Until the end of the therapy, the value is constantly above the alarm limit of 75 ml/min.

Using the online determination of the internal filtration, the progress of the latter can be indicated throughout the entire therapy and it is possible to adapt treatment parameters so as to maintain this filtration.

The invention claimed is:

1. An apparatus for the purification of blood, comprising:
   a purification device through which blood and cleaning fluid can flow;
   at least one blood pressure sensor for measuring pressures of the blood at a blood input and/or a blood output of the purification device;
   at least one cleaning fluid (CF) pressure sensor for detecting pressures of the cleaning fluid at a CF input and/or a CF output of the purification device;
   a determination device configured to:
      determine a blood pressure profile based on the measured pressures of the blood at the blood input and/or the blood output of the purification device,
      determine a cleaning fluid pressure profile based on the measured pressures of the cleaning fluid at the CF input and/or the CF output of the purification device,
      determine a pressure intersection made up of the blood pressure profile and the cleaning fluid pressure profile,
      calculate a median transmembrane pressure for the filtration from the determined pressure intersection,
      calculate an internal convection value in the purification device on the basis of the calculated median transmembrane pressure; and
   a control unit configured to adjust an internal convection of the purification device by comparing the calculated internal convection value with a predefined target value and by adapting the flow of the blood to be cleaned and/or the flow of the cleaning fluid to match the calculated internal convection value to the predefined target value.

2. The apparatus according to claim 1, wherein the determination device is further configured to:
   determine the flows of a cleaning fluid and/or of the blood,
   ascertain pressure differences in the purification device on the basis of the determined flows by calculation or with the aid of characteristic curves or value tables which are specific to the dialyzer and have been stored in advance, and
   incorporate the ascertained pressure differences into the calculation of the internal convection value in the purification device.

3. The apparatus according to claim 1, in which the determination device additionally effects a hematocrit determination or a hematocrit presetting.

4. The apparatus according to claim 1, further comprising a display configured to display the determined internal convection.

5. The apparatus according to claim 1, wherein the internal convection value is calculated on the further basis of an ultrafiltration coefficient as a product of a filter surface and a permeability.

6. The apparatus of claim 1, wherein the determination device is further configured to effect a determination or presetting of a plasma viscosity or of a plasma protein concentration.

7. The apparatus of claim 1, wherein the cleaning fluid is dialysis fluid.

8. A method for an extracorporeal purification of blood, comprising:
   conveying, through a purification device, the blood and a cleaning fluid;
   measuring, with at least one blood pressure sensor, pressures of the blood at a blood input and/or a blood output of the purification device;
   measuring, with at least one cleaning fluid (CF) pressure sensor, pressures of the cleaning fluid at the CF input and/or the CF output of the purification device;
   determining, with a determination device, a blood pressure profile based on the measured pressures of the blood at the blood input and/or the blood output of the purification device,
   determining, with the determination device, a cleaning fluid pressure profile based on the measured pressures of the cleaning fluid at the CF input and/or the CF output of the purification device,
   determining, with the determination device, a pressure intersection made up of the blood pressure profile and the cleaning fluid pressure profile,
   calculating, with the determination device, a median transmembrane pressure for the filtration from the determined pressure intersection,
   calculating, with the determination device, an internal convection value in the purification device on the basis of the calculated median transmembrane pressure, and
   adjusting, with a control unit, an internal convection of the purification device, by comparing the calculated internal convection value with a predefined target value and adapting the flow of the blood to be cleaned and/or the flow of the cleaning fluid to match the calculated internal convection value to the predefined target value.

9. The method according to claim 8, in which a blood purification is carried out in the form of a hemodialysis or a hemodiafiltration and the method further comprises:
   determining, with the determination device, flows of the blood and the cleaning fluid,
   ascertaining, with the determination device, pressure differences in the purification device on the basis of the determined flows by calculation or with the aid of characteristic curves or value tables which are specific to the dialyzer and have been stored in advance, and
   incorporating, with the determination device, the ascertained pressure difference into the step of calculating the internal convection value in the purification device.

10. The method according to claim 8, further comprising carrying out, with the determination device, a hematocrit determination or hematocrit presetting.

11. The method of claim 8, wherein the internal convection value is further calculated in consideration of an ultrafiltration coefficient as a product of the filter surface and the permeability.

12. The method of claim 8, wherein the cleaning fluid is dialysis fluid.

13. The method of claim 8, wherein the method further comprises determining or presetting, with the determination device, a plasma viscosity or a plasma protein concentration.

* * * * *